US009931109B2

(12) United States Patent
Burckhardt et al.

(10) Patent No.: US 9,931,109 B2
(45) Date of Patent: Apr. 3, 2018

(54) RETRACTOR AND TOOLS FOR IMPLANTATION OF ELECTRICAL STIMULATION LEADS AND METHODS OF USING AND MANUFACTURE

(71) Applicant: Boston Scientific Neuromodulation Corporation, Valencia, CA (US)

(72) Inventors: Laura Burckhardt, Union City, CA (US); Michael X. Govea, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 204 days.

(21) Appl. No.: 15/019,848

(22) Filed: Feb. 9, 2016

(65) Prior Publication Data
US 2016/0235394 A1    Aug. 18, 2016

Related U.S. Application Data

(60) Provisional application No. 62/116,018, filed on Feb. 13, 2015.

(51) Int. Cl.
*A61B 17/02* (2006.01)
*A61N 1/05* (2006.01)
(Continued)

(52) U.S. Cl.
CPC ........ *A61B 17/0218* (2013.01); *A61N 1/0553* (2013.01); *A61N 1/372* (2013.01);
(Continued)

(58) Field of Classification Search
CPC .............. A61B 17/0218; A61N 1/0553; A61N 1/37205; A61N 1/372
See application file for complete search history.

(56) References Cited

U.S. PATENT DOCUMENTS 3,330,278 A    7/1967   Santomieri
3,359,978 A   12/1967   Smith
(Continued)

FOREIGN PATENT DOCUMENTS

EP    2008686    12/2008
WO   89/00436    1/1989
(Continued)

OTHER PUBLICATIONS

International Search Report and Written Opinion for PCT/US2016/017191 dated Jun. 6, 2015.
U.S. Appl. No. 62/153,844, filed Apr. 28, 2015.

*Primary Examiner* — Christian Sevilla
(74) *Attorney, Agent, or Firm* — Lowe Graham Jones PLLC; Bruce E. Black

(57) ABSTRACT

A retractor for implanting a paddle lead of an electrical stimulation system includes a shaft defining a length, an interior lumen, a first end for receiving tools or paddle lead, and a second end opposite the first end and configured and arranged for insertion into tissue of a patient; a handle coupled to the shaft; and at least one divider disposed within the interior lumen and dividing a portion of the interior lumen into at least two compartments, wherein the at least one divider extends from at or near the first end of the shaft and no more than 70% of the length of the shaft. At least one of the compartments is sized for implantation of a paddle lead of an electrical stimulation system therethrough.

15 Claims, 8 Drawing Sheets

(51) Int. Cl.
  *A61N 1/372* (2006.01)
  *A61B 17/34* (2006.01)
  *A61B 17/00* (2006.01)

(52) U.S. Cl.
  CPC ... *A61B 17/3468* (2013.01); *A61B 2017/0046* (2013.01); *A61B 2017/00876* (2013.01); *A61B 2017/3445* (2013.01)

(56) References Cited

U.S. PATENT DOCUMENTS

| | | |
|---|---|---|
| 3,568,660 A | 3/1971 | Crites et al. |
| 3,677,243 A | 7/1972 | Nerz |
| 4,166,469 A | 9/1979 | Littleford |
| 4,355,646 A | 10/1982 | Kallok et al. |
| 4,449,973 A | 5/1984 | Luther |
| RE31,855 E | 3/1985 | Osborne |
| 4,512,351 A | 4/1985 | Pohndorf |
| 4,608,986 A | 9/1986 | Beranek et al. |
| 4,808,157 A | 2/1989 | Coombs |
| 5,125,904 A | 6/1992 | Lee |
| 5,312,355 A | 5/1994 | Lee |
| 5,320,602 A | 6/1994 | Karpiel |
| 5,380,290 A | 1/1995 | Makower et al. |
| 5,409,469 A | 4/1995 | Schaerf |
| 5,441,504 A | 8/1995 | Pohndorf et al. |
| 5,713,867 A | 2/1998 | Morris |
| 5,741,233 A | 4/1998 | Riddle et al. |
| 5,752,937 A | 5/1998 | Otten et al. |
| 5,755,693 A | 5/1998 | Walker et al. |
| 5,931,863 A | 8/1999 | Griffin, III et al. |
| 6,080,141 A | 6/2000 | Castro et al. |
| 6,181,969 B1 | 1/2001 | Gord |
| 6,251,119 B1 | 6/2001 | Addis |
| 6,358,460 B1 | 3/2002 | Hunt, Jr. et al. |
| 6,454,744 B1 | 9/2002 | Spohn et al. |
| 6,494,860 B2 | 12/2002 | Rocamora et al. |
| 6,516,227 B1 | 2/2003 | Meadows et al. |
| 6,582,390 B1 | 6/2003 | Sanderson |
| 6,609,029 B1 | 8/2003 | Mann et al. |
| 6,609,032 B1 | 9/2003 | Woods et al. |
| 6,641,564 B1 | 11/2003 | Kraus |
| 6,645,178 B1 | 11/2003 | Junker et al. |
| 6,712,791 B2 | 3/2004 | Lui et al. |
| 6,741,892 B1 | 5/2004 | Meadows et al. |
| 6,749,600 B1 | 6/2004 | Levy |
| 6,758,854 B1 | 7/2004 | Butler et al. |
| 6,869,416 B2 | 3/2005 | Windheuser et al. |
| 6,939,327 B2 | 9/2005 | Hall et al. |
| 7,001,396 B2 | 2/2006 | Glazier et al. |
| 7,014,626 B2 | 3/2006 | Sanderson |
| 7,101,353 B2 | 9/2006 | Lui et al. |
| 7,192,433 B2 | 3/2007 | Osypka et al. |
| 7,244,150 B1 | 7/2007 | Brase |
| 7,359,755 B2 | 4/2008 | Jones et al. |
| 7,437,193 B2 | 10/2008 | Parramon |
| 7,524,305 B2 | 4/2009 | Moyer |
| 7,672,734 B2 | 3/2010 | Anderson |
| 7,744,571 B2 | 6/2010 | Fisher et al. |
| 7,761,165 B1 | 7/2010 | He |
| 7,887,733 B2 | 2/2011 | Moyer |
| 7,909,798 B2 | 3/2011 | Osypka |
| 7,938,806 B2 | 5/2011 | Fisher et al. |
| 7,941,227 B2 | 5/2011 | Barker |
| 7,949,395 B2 | 5/2011 | Kuzma |
| 7,974,706 B2 | 7/2011 | Moffitt et al. |
| 7,985,232 B2 | 7/2011 | Potter et al. |
| 7,993,305 B2 | 8/2011 | Ye et al. |
| 8,043,263 B2 | 10/2011 | Helgeson et al. |
| 8,105,287 B2 | 1/2012 | Fisher et al. |
| 8,105,315 B2 | 1/2012 | Johnson et al. |
| 8,112,159 B2 | 2/2012 | Harris et al. |
| 8,147,456 B2 | 4/2012 | Fisher et al. |
| 8,175,710 B2 | 5/2012 | He |
| 8,224,450 B2 | 7/2012 | Brase |
| 8,273,059 B2 | 9/2012 | Nardeo et al. |
| 8,348,899 B2 | 1/2013 | Chesnin et al. |
| 8,364,278 B2 | 1/2013 | Pianca et al. |
| 8,377,006 B2 | 2/2013 | Tal et al. |
| 8,382,715 B2 | 2/2013 | Nardeo et al. |
| 8,849,422 B2 | 9/2014 | Pianca |
| 2002/0111617 A1 | 8/2002 | Cosman et al. |
| 2003/0028179 A1* | 2/2003 | Piskun ............ A61B 17/06066 606/1 |
| 2003/0032975 A1* | 2/2003 | Bonutti ............ A61B 17/0218 606/192 |
| 2003/0073998 A1* | 4/2003 | Pagliuca ........... A61B 17/0218 606/86 A |
| 2005/0021119 A1 | 1/2005 | Sage et al. |
| 2005/0055027 A1 | 3/2005 | Yeung et al. |
| 2005/0107861 A1 | 5/2005 | Harris et al. |
| 2005/0113860 A1 | 5/2005 | Keidar |
| 2006/0047185 A1* | 3/2006 | Shener ............. A61B 1/00068 600/156 |
| 2006/0200186 A1* | 9/2006 | Marchek .......... A61B 17/0218 606/191 |
| 2006/0206008 A1* | 9/2006 | Dalton ............. A61B 17/0218 600/215 |
| 2007/0150036 A1 | 6/2007 | Anderson |
| 2008/0300538 A1 | 12/2008 | Schweikert et al. |
| 2009/0248111 A1 | 10/2009 | Pianca et al. |
| 2009/0254019 A1 | 10/2009 | Gehl et al. |
| 2009/0259283 A1 | 10/2009 | Brandt et al. |
| 2010/0312319 A1* | 12/2010 | Barker ............. A61N 1/0553 607/117 |
| 2011/0054402 A1 | 3/2011 | Tanabe et al. |
| 2011/0218549 A1 | 9/2011 | Barker |
| 2011/0224680 A1 | 9/2011 | Barker |
| 2011/0224681 A1 | 9/2011 | McDonald |
| 2011/0230893 A1 | 9/2011 | Barker |
| 2012/0202928 A1 | 8/2012 | Barker et al. |
| 2012/0209285 A1 | 8/2012 | Barker et al. |
| 2012/0323254 A1 | 12/2012 | Bonde et al. |
| 2013/0053851 A1 | 2/2013 | Schmitz et al. |
| 2014/0039586 A1 | 2/2014 | Barker et al. |
| 2014/0073926 A1 | 3/2014 | Rajendran et al. |
| 2014/0276927 A1 | 9/2014 | Barker |
| 2015/0073431 A1 | 3/2015 | Barker |
| 2015/0073432 A1 | 3/2015 | Barker |

FOREIGN PATENT DOCUMENTS

| | | |
|---|---|---|
| WO | 03011361 | 2/2003 |
| WO | 2006/135753 | 12/2006 |

\* cited by examiner

RETRACTOR AND TOOLS FOR IMPLANTATION OF ELECTRICAL STIMULATION LEADS AND METHODS OF USING AND MANUFACTURE

CROSS-REFERENCE TO RELATED APPLICATIONS

This application claims the benefit under 35 U.S.C. § 119(e) of U.S. Provisional Patent Application Ser. No. 62/116,018, filed Feb. 13, 2015, which is incorporated herein by reference.

FIELD

The present invention is directed to the area of implantable electrical stimulation systems and methods of making and using the systems. The present invention is also directed to retractors and tools for the implantation of electrical stimulation leads, as well as methods of making and using the retractors, tools, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a retractor for implanting a paddle lead of an electrical stimulation system. The retractor includes a shaft defining a length, an interior lumen, a first end for receiving tools or the paddle lead, and a second end opposite the first end and configured and arranged for insertion into tissue of a patient; a handle coupled to the shaft; and at least one divider disposed within the interior lumen and dividing a portion of the interior lumen into at least two compartments, wherein the at least one divider extends from at or near the first end of the shaft and no more than 70% of the length of the shaft. At least one of the compartments is sized for implantation of a paddle lead of an electrical stimulation system therethrough.

In at least some embodiments, the at least one divider extends at least 40% of the length of the shaft. In at least some embodiments, the at least one divider is two dividers that divide the portion of the interior lumen into three compartments. In at least some embodiments, the three compartments form two side ports and a central port disposed between the two side ports. In at least some embodiments, the central port is larger than either of the two side ports and the central port is sized for implantation of the paddle lead of the electrical stimulation system therethrough.

Another embodiment is an implantation kit that includes any of the retractors described above; and an electrical stimulation lead, including a paddle body, at least one lead body having a distal end portion, a proximal end portion, and a longitudinal length, the distal end of each of the at least one lead body coupled to the paddle body, electrodes disposed in at least two columns on the paddle body, terminals disposed along the proximal end portion of each of the at least one lead body, and conductors electrically coupling the terminals to the electrodes, where at least one of the compartments is sized for implantation of the paddle lead therethrough.

In at least some embodiments, the retractor or the implantation kit includes a filler configured and arranged for insertion into the shaft of the retractor. The filler includes a handle and filler fingers coupled to the handle and configured and arranged to substantially fill the shaft of the retractor. The finer fingers are separated by at least one gap configured and arranged to align with the at least one divider of the retractor when the filler is inserted into the retractor.

In at least some embodiments, the retractor or the implantation kit includes at least one blade tool. Each blade tool includes an actuator, a rod coupled to the actuator, and a blade movably coupled to the rod and configured and arranged to move back and forth in response to the actuator. Each blade tool is configured and arranged so that the blade and rod can be inserted through the first end of the shaft into one of the compartments of the shaft of the retractor and the blade can be extended out of the second end of the shaft.

In at least some embodiments, the retractor or the implantation kit includes an actuator tool configured and arranged for insertion through the first end of the retractor into one of the compartments of the shaft of the retractor; and at least one blade tool. Each blade tool includes a handle, a rod coupled to the handle, and a blade movably coupled to the rod and configured and arranged to move back and forth in response to the actuator tool. Each blade tool is configured and arranged so that the blade and rod can be inserted through the first end of the shaft into one of the compartments of the shaft of the retractor and the blade can be extended out of the second end of the shaft. In at least some embodiments, the blade of each of the at least one blade tool has a first magnetic polarity and the actuator tool has a second magnetic polarity opposite the first magnetic polarity.

In at least some embodiments that include a blade tool, the at least one divider is two dividers that divide the portion of the interior lumen into three compartments and the at least one blade tool is two blade tools.

In at least some embodiments, the implantation kit also includes a series of introducers, wherein each introducer in the series has a diameter larger than a preceding one of the introducers in the series. In at least some embodiments, the implantation kit also includes a control module coupleable to the electrical stimulation lead. In at least some embodiments, the implantation kit also includes a lead extension coupleable to the control module and the electrical stimulation lead.

Another embodiment is a method of implanting an electrical stimulation lead. The method includes providing any of the implantation kits described above; inserting the second end of the retractor into tissue of the patient; and implanting the paddle body of the electrical stimulation lead into the patient through one of the at least one compartment of the retractor.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to retractors and tools for the implantation of electrical stimulation leads, as well as methods of making and using the retractors, tools, and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; and 7,761,165; 7,974,706; and U.S. Pat. Nos. 8,175,710; 8,224,450; 8,364,278; U.S. Patent Application Publication No. 2007/0150036, all of which are incorporated by reference.

Figure 1:
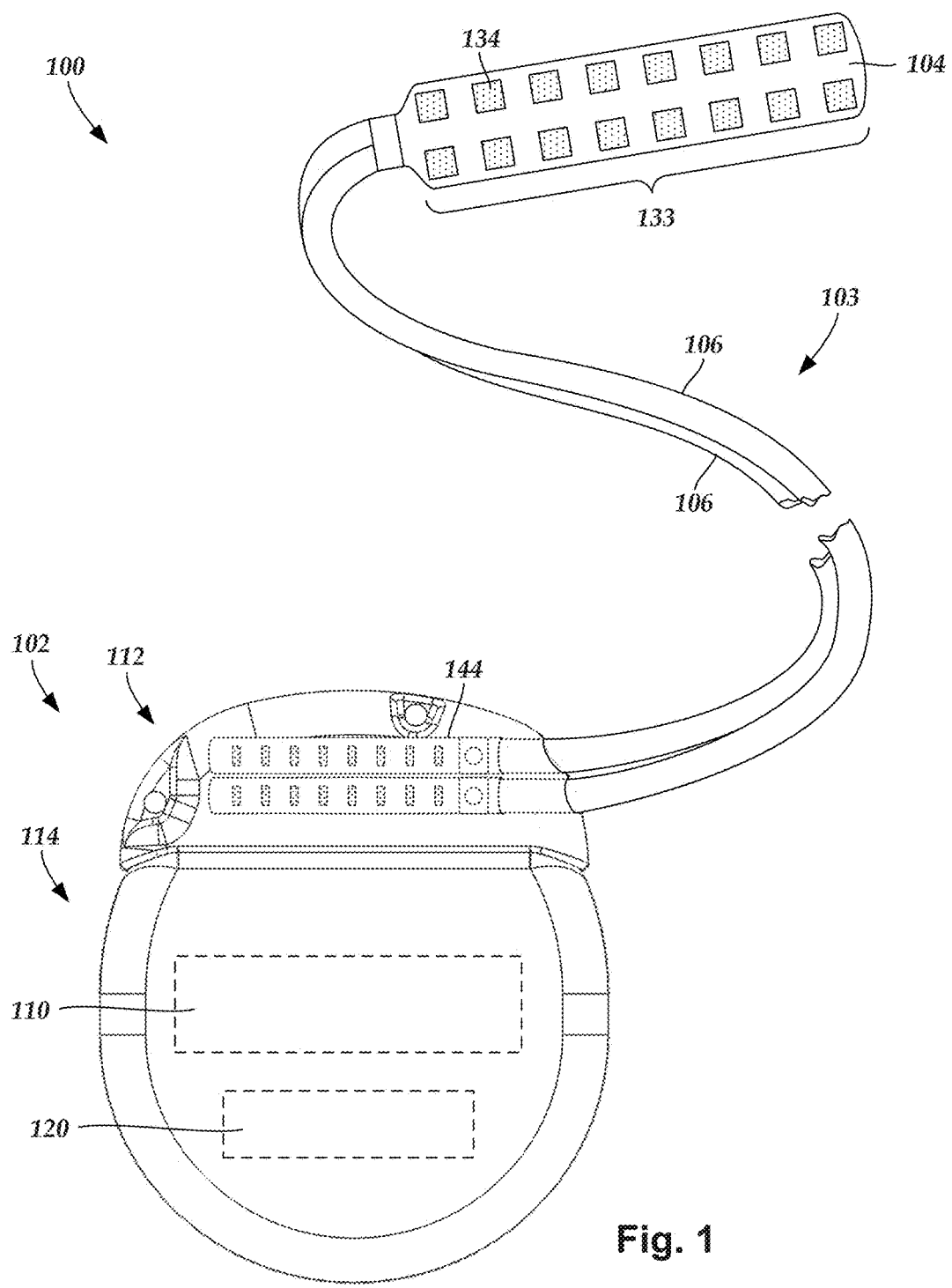
FIG. 1 is a schematic side view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 2. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 10 in FIG. 2A-B) is disposed along each of the one or more lead bodies 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices. For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 10 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the paddle body including, for example, four, five, six, seven, eight, nine, ten, eleven, twelve, fourteen, sixteen, twenty-four, thirty-two, or more electrodes 134. The electrodes 134 can be disposed on the paddle body 104 in any suitable arrangement. In FIG. 1, the electrodes 134 are arranged into two columns, where each column has eight electrodes 134.

The electrodes of the paddle body 104 are typically disposed in, or separated by, a non-conductive, biocompatible material such as, for example, silicone, polyurethane, polyetheretherketone ("PEEK"), epoxy, and the like or combinations thereof. The paddle body 104 and the one or more lead bodies 106 may be formed in the desired shape by any process including, for example, molding (including injection molding), casting, and the like. The non-conductive material typically extends from the paddle body 104 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Figure 2A:
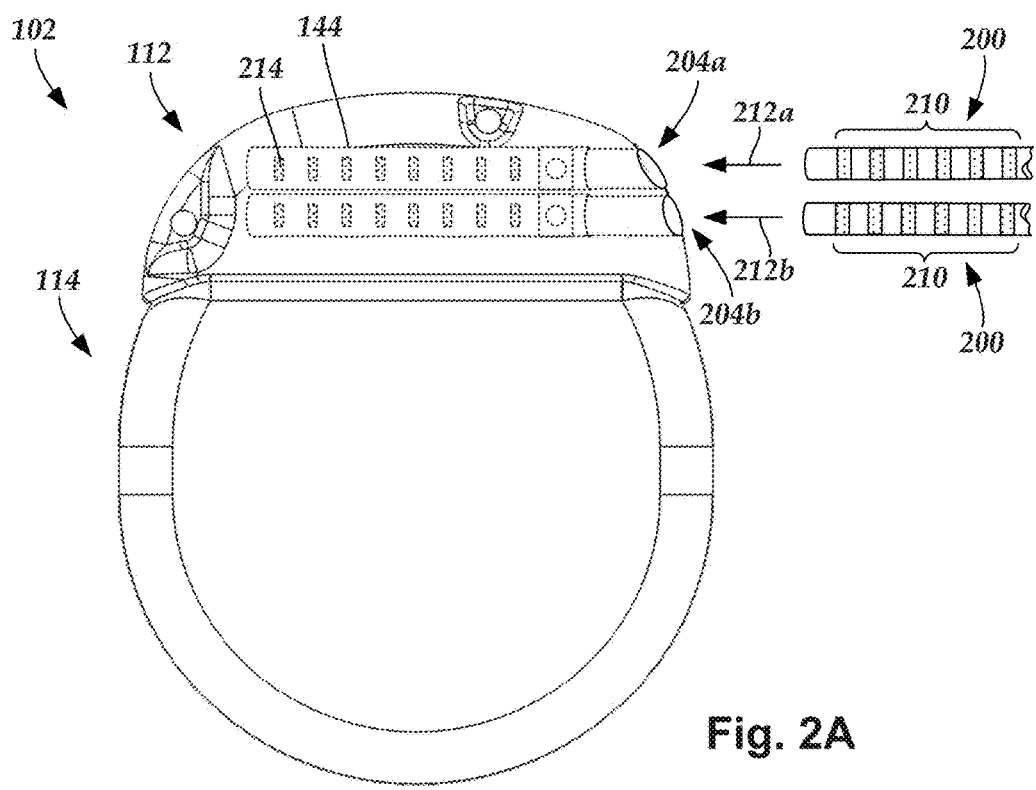
FIG. 2A is a schematic side view of one embodiment of the control module of FIG. 1 configured and arranged to electrically couple to an elongated device, according to the invention.
Figure 2B:
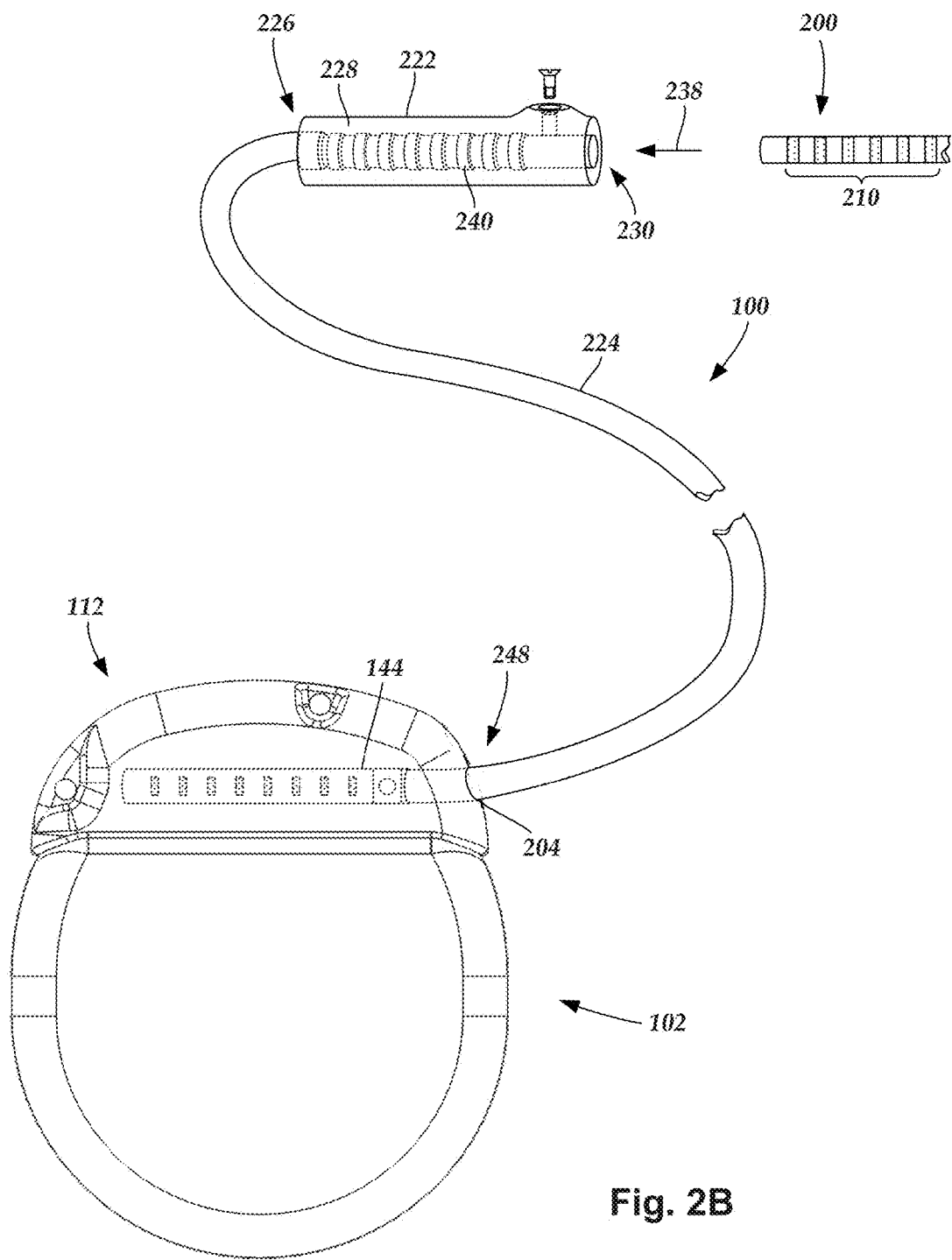
FIG. 2B is a schematic side view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B). The connector contacts are disposed in connectors (e.g., 144 in FIGS. 1-2B; and 222 FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors" y be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like in at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, one or more of the lead bodies 106 of FIG. 1, one or more intermediate devices (e.g., a splitter, the lead extension 224 of FIG. 2B, an adaptor, or the like or combinations thereof, or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., one of the lead bodies 106 of FIG. 1, a splitter, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144 (e.g., the ports 204a and 204b of FIG. 1), or to receive multiple elongated devices 200 (e.g., both of the lead bodies 106 of FIG. 1), or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Paddle leads are often implanted into the spinal cord by laminectomy or laminotomy techniques. It is desirable, however, to identify other implantation methods that are less invasive. Such less invasive methods can have one or more advantages such as, for example, less patient or tissue trauma, a lower risk of infection, less healing time, less scarring, less surgical time, or any combination thereof. Tools can be developed to assist in percutaneous delivery and implantation of paddle leads.

Figure 7A:
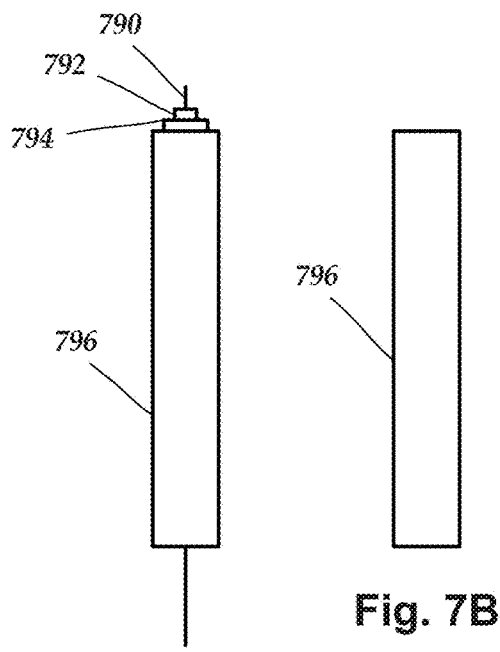
FIG. 7A is a schematic side view of one embodiment of a guide wire and series of introducers for use with a retractor, according to the invention.
Figure 7B:
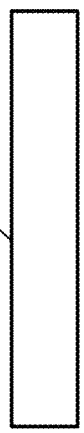
FIG. 7B is a schematic side view of one of the introducers of FIG. 7A with the guide wire and other introducers removed, according to the invention.

As described herein, a retractor tool can be used for delivery and implantation of a paddle lead. In at least some embodiments, a guide wire 790 can be inserted in the patient and a series of two or more introducers 792, 794, 796 (for example, dilators, needles, or the like) can be sequentially introduced over the guide wire 790 and used to create an opening through the tissue for the retractor, as illustrated in FIG. 7A. The introducers in the series have increasing diameter. The smallest diameter introducer 792 is inserted first over the guide wire 790 through the tissue and then each succeeding introducer in the series is inserted over one or more of the preceding introducers to increase the size of the opening through the tissue. An example of the use of series of introducers can be found at U.S. Pat. No. 8,849,422, incorporated herein by reference. Each preceding introducer can be removed after inserting the next introducer in the series or the preceding introducers can be removed together after the last introducer 796 is inserted over the guide wire 790 leaving the last introducer 796, as illustrated in FIG. 7B. Optionally, a sheath can be inserted into the introducer 796 and the introducer may then be removed. The last introducer 796 or sheath can then be used for insertion of other surgical instruments such as the retractor described below. In other embodiments, a sheath is not used and the retractor or other surgical instrument is inserted through the last introducer.

Figure 3A:
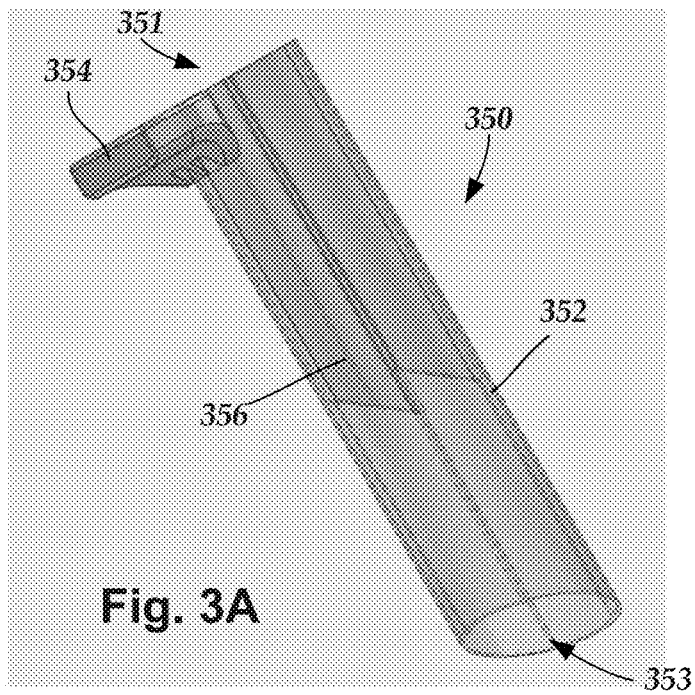
FIG. 3A is a schematic perspective view of one embodiment of a retractor for implanting a paddle lead, according to the invention.
Figure 3B:
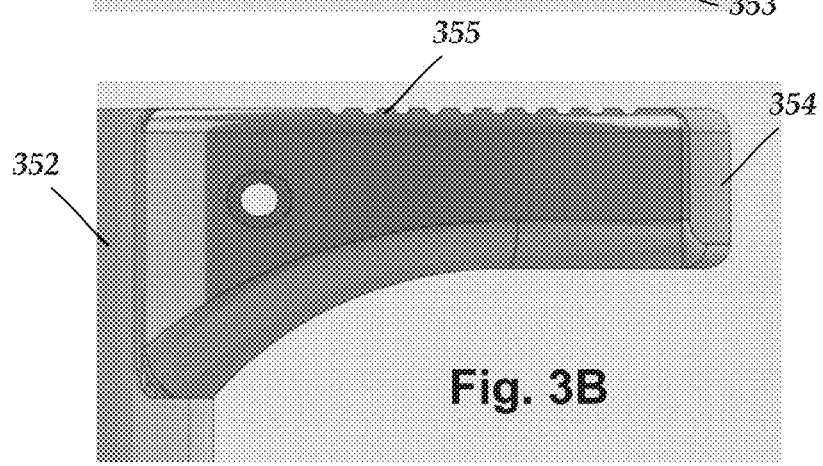
FIG. 3B is a schematic perspective view of the handle and a portion of the shaft of the retractor of FIG. 3A, according to the invention.
Figure 3C:
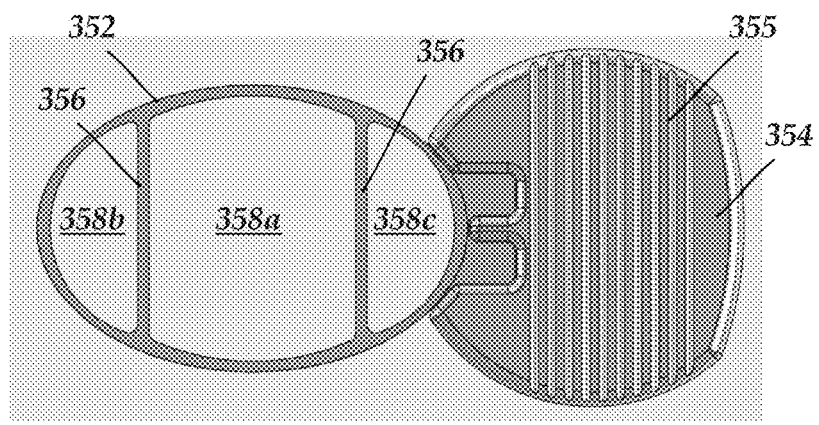
FIG. 3C is a schematic top view of the retractor of FIG. 3A, according to the invention.

FIGS. 3A-3C illustrate one embodiment of a retractor 350 that includes a shaft 352, a handle 354, and at least one divider 356 which extends from the top 351 of the shaft at least partway down the shaft. The bottom 353 of the shaft 352 can be beveled to aid in insertion and can also be sharpened. The shaft 352 has an oval or circular cross-sectional shape and is divided at the top 351 of (and at least partway down) the shaft into two or more compartments 358a, 358b, 358c by the one or more dividers 356, as illustrated in FIG. 3C. In the illustrated embodiment, the compartment 358a is a middle port and the compartments 358b, 358c are two side ports. The two side ports may be equal in size (e.g., volume or cross-sectional area) or may differ in size. In some embodiments, the middle port is equal in size with one or more of the side port(s). In other embodiments, the middle port is larger in size than each side port. The top 351 of the shaft 352 receives tools or a paddle lead and the bottom 353 of the shaft 352 is designed for insertion into tissue of a patient.

The retractor 350 can have any suitable number of dividers 356 including, but not limited to, one, two, or three dividers. In at least some embodiments, the one or more dividers 356 extend at least 30%, 40%, 45%, 50%, 55%, 60%, 66%, 70%, or 75% of the length of the shaft 352. In at least some embodiments, the one or more dividers 356 extend no more than 75%, 70%, 66%, 60%, or 50% of the length of the shaft. In some embodiments with multiple dividers, all of the dividers extend the same distance along the length of the shaft. In other embodiments with multiple dividers, the dividers extend different distances along the length of the shaft. In the illustrated embodiment, the one or more dividers 356 extend to the top 351 of the shaft 352. In other embodiments, the one or more dividers 356 may terminate before the top 351 of the shaft 352. In some embodiments, the one or more dividers 356 may be removable from the shaft 352. In other embodiments, the one or more dividers 356 are not removable from the shaft 352 and may be integrally formed as a single piece with the shaft 352.

The handle 354 is coupled to the top 351 (or near the top) of the shaft 352. In some embodiments, the handle 354 is removable from the shaft 352 and may be, for example, snap fit or otherwise removably attached to the shaft. A removable handle may be useful if the introducer is to be removed over the retractor. In other embodiments, the handle 354 is non-removably attached to the shaft 352 and may be integrally formed as a single piece with the shaft. In at least some embodiments, the handle 354 can include grooves 355, ridges, dimples, or other surface roughening or surface features to facilitate gripping of the handle or to provide a tactile feel to the handle.

The shaft 352 can be made of any suitable material including, but not limited to, metal, plastic, or any combination thereof. The handle 354 and one or more dividers 356 can be made of the same material as the shaft 352 or different materials. In at least some embodiments, the shaft has a length in the range of 3 to 6 inches (about 7.5 to 15 cm), although other lengths can be used and may depend on the implantation site. In some embodiments the shaft has a fixed length and in other embodiments the length of the shaft may be varied, for example, if the shaft contains telescoping sections. In at least some embodiments, the shaft 352 has transverse cross-sectional diameters in a range of 0.5 to 4 inches (about 1.2 to 0.2 cm) or in a range of 1 to 3 inches (about 2.5 to 7.6 cm) or in a range of 1 to 2.5 inches (about 2.5 to 6.3 cm), although other transverse cross-sectional diameters can be used and may depend on the implantation site or the width of the paddle lead. In one embodiment, the compartment 358a has cross-sectional dimensions of 1.5 inches (about 3.8 cm) by 1 inch (about 2.5 cm), although other embodiments may have different dimensions. In at least some embodiments, the bottom 353 of the shaft 352 is angle in a range of 10 to 40 degrees or in a range of 15 to 35 degrees, although other angles (or no angle at all) can also be used.

In at least some embodiments, a filler is inserted into the shaft of the retractor during insertion of the shaft into the body of the patient to prevent or reduce coring of tissue by the shaft. It will be recognized that in other embodiments, a filler is not inserted into the retractor when the retractor is inserted into the patient. In particular, the filler may not be needed if the introducers sufficiently open up the patient or reduce the likelihood or effects of tissue coring.

Figure 4A:
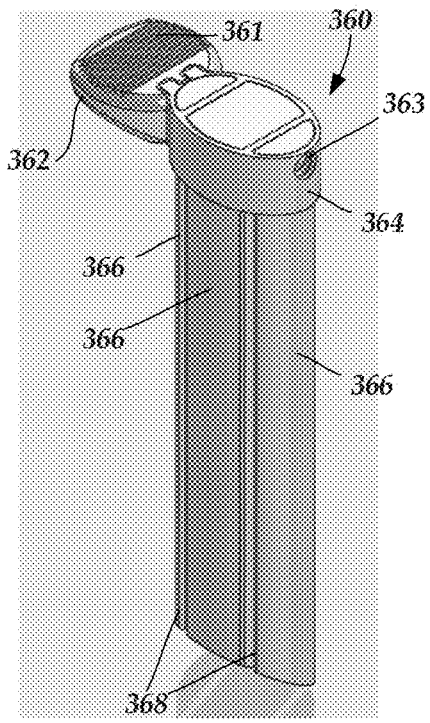
FIG. 4A is a schematic perspective view of one embodiment of a filler for insertion into the retractor of FIG. 3A, according to the invention.
Figure 4B:
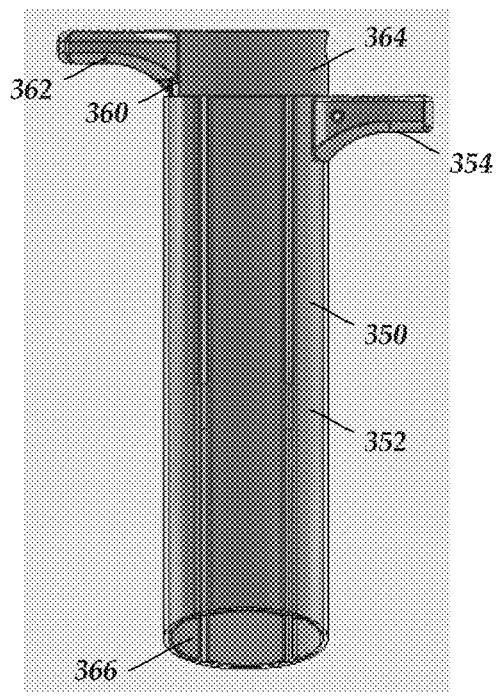
FIG. 4B is a schematic side view of the filler of FIG. 4A inserted into e retractor of FIG. 3A, according to the invention.

FIG. 4A illustrates one embodiment of a filler 360 that includes a handle 362, a collar 364, and two or more filler fingers 366 that are spaced apart by one or more gaps 368. FIG. 4B illustrates the filler 360 inserted into shaft 352 of the retractor 350 of FIG. 3A. The finer fingers 366 of the filler 360 substantially fills the compartments of the shaft 352, particularly near the bottom 353 (FIG. 3A) of the shaft. The one or more gaps 368 of the filler 360 align with the one or more dividers 356 of the retractor 350. As illustrated in FIG. 4B, the collar 364 of the filler 360 can sit on top of the retractor 350. In other embodiments, the collar may fit within the retractor. In at least some embodiments, the handle 362 of the filler 360 is disposed opposite of the handle 354 of the retractor 350, although in other embodiments the two handles may be disposed with one over the other or in any other arrangement.

The filler fingers 366 can be made of any suitable material including, but not limited to, metal, plastic, or any combination thereof. The collar 364 and handle 362 of the filler 360 can be made of the same material as the filler fingers 366 or different materials. If the shall 352 is beveled, the filler fingers 366 may be similarly beveled.

The handle 362 is coupled to the collar 364 of the filler 360. In some embodiments, the handle 362 is removable from the collar 364 and may be for example, snap fit or otherwise removably attached to the collar. In other embodiments, the handle 362 is non-removably attached to the collar 364 and may be integrally formed with the collar. In at least some embodiments, the handle 362 can include grooves 361, ridges, dimples, or other surface roughening or surface features to facilitate gripping of the handle or to provide a tactile feel to the handle. In some embodiments, the filler fingers 366 are removable from the collar 364 and may be, for example, snap fit, attached with a fastener 363 (e.g.; a screw; bolt; or nut); or otherwise removably attached to the collar. In other embodiments, the filler fingers are non-removably attached to the collar 364 and may be integrally formed with the collar.

With the filler 360 removed, the paddle lead can be implanted through one of the compartments 358a, 358b, 358c of the retractor 350. In at least some embodiments, the paddle lead is implanted through the center port of compartment 358a, but implantation through one of the side ports of compartments 358b, 358c may be possible if those ports are of sufficient size.

In addition to implantation of the paddle lead, the compartments 358a, 358b, 358c can also be used for insertion of one or more tools, sensors, test equipment or probes, or other devices into the patient. Examples include, but are not limited to, a hook or other mechanism to secure the retractor to tissue (for example, a hook or other securing mechanism through one or both of the side ports), an endoscope, a light, kerrison ronguer, curette, drill, suturing device (such as the FIXATE™ Suturing Device from Boston Scientific Corporation), lead anchor, medication delivery catheter or needle, tissue or fluid extractor, cautery instruments, paddle lead-specific delivery tools, or the like.

One example of a tool is a blade tool that can be used to remove, dissect, or retract tissue at the bottom of the retractor. In at least some embodiments, a pair of blade tools can be used in combination.

Figure 5A:
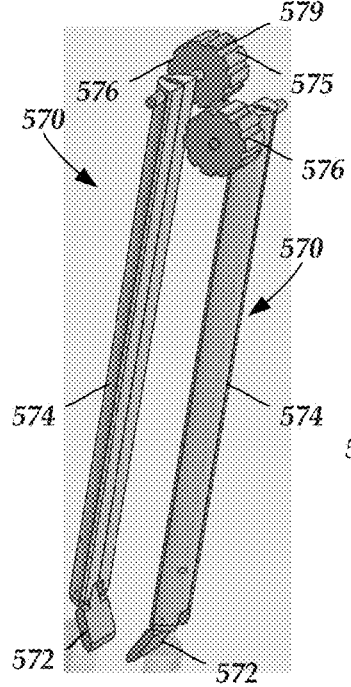
FIG. 5A is a schematic perspective view of one embodiment of a pair of blade tools for use with the retractor of FIG. 3A, according to the invention.

FIG. 5A illustrates one embodiment of a pair of blade tools 570. Each blade tool 570 includes a blade 572, a rod 574, and an actuator 576. The blade 572 is articulated and movably attached to the rod 574 using, for example, an axle 573 (FIG. 5C), hinge, or other attachment mechanism that allows the blade to move back and forth relative to the rod. In at least some embodiments, the blade 572 can sweep at least 60, 75, 90, 100, 120, 150, or 180 degrees.

The actuator 576 is attached to the rod 574 and operates a mechanism, such as a cable 578 (FIGS. 5B and 5C) that extends along the rod and is attached to the blade 572 to move the blade back and forth. The illustrated embodiment of FIG. 5A uses a rotatable knob 575 coupled to an axle 577 as the actuator 576, but any other suitable actuator (for example, an electrically controlled actuator) can be used. In at least some embodiments, the knob 575 can include grooves 579, ridges, dimples, or other surface roughening or surface features to facilitate rotation of the knob or to provide a tactile feel to the knob.

Figure 5B:
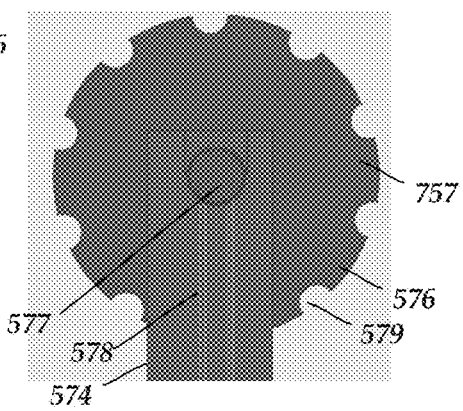
FIG. 5B is a schematic side view of a top portion of the blade tool of FIG. 5A including a knob, axle, rod, and cable, according to the invention.
Figure 5C:
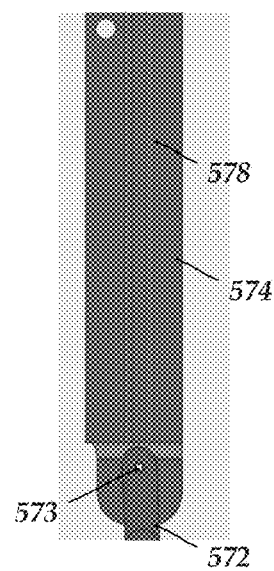
FIG. 5C is a schematic side view of a bottom portion of the blade toot of FIG. 5A including a portion of the blade, axle, rod, and cable, according to the invention.

In the illustrated embodiment, the cable 578 is coupled to the axle 577, as illustrated in FIG. 5B, and the hinge 573, as illustrated in FIG. 5C, so that rotation of the knob 575 moves the cable 578 to operate the blade 572. The components of the blade tool can be made of metal, plastic, or any other suitable material, or any combination thereof.

Figure 5D:
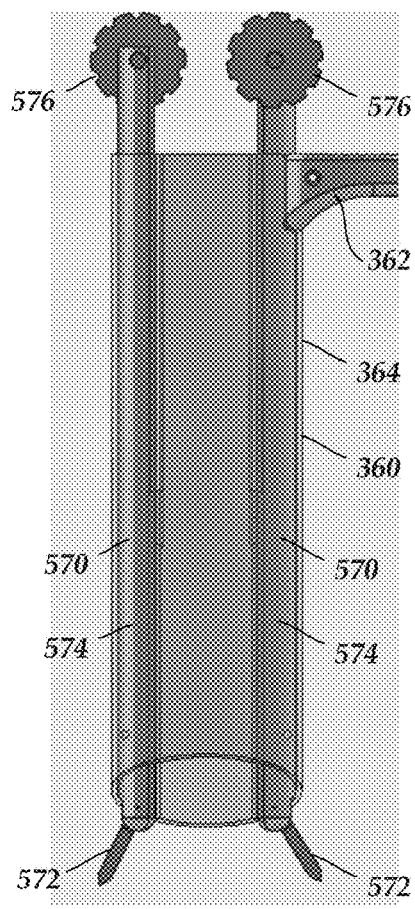
FIG. 5D is a schematic side view of the blade tools of FIG. 5A inserted into the retractor of FIG. 3A, according to the invention.
Figure 5E:
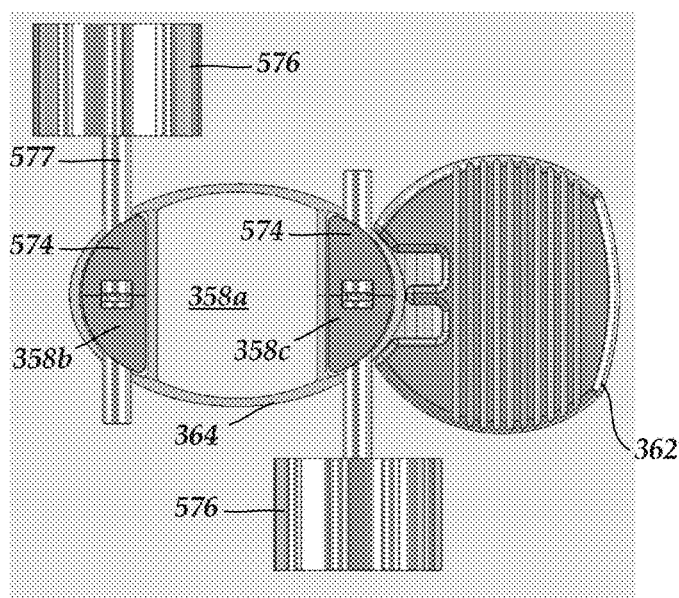
FIG. 5E is a schema c top view of the blade tools and retractor of FIG. 5D, according to the invention.

FIGS. 5D (side view) and 5E (top view) illustrate the blade tools 570 disposed in compartments 358b, 358c of retractor 350. In at least some embodiments, the blades 572 of the blade tools 570 are sufficiently long so that the blades 572 can sweep out most or all of the region beneath the retractor 350, as illustrated in FIG. 5D, to remove, dissect, or retract tissue from that region to facilitate implantation of the paddle lead through compartment 358a of the retractor.

In at least some embodiments, different blades 570 or different blade tools 570 can be used for different functions. For example, one set of blades 570 may dissect tissue and another set of blades may move the tissue away from the opening in the shaft 352 of the retractor 350.

FIGS. 6A-6D illustrate another embodiment of a pair of blade tools 670 disposed in the retractor 350 that utilize magnetic blades 672 disposed on rods 674 with handles 678 attached to the rods 674. The blade 672 is movably attached to the rod 674 using, for example, an axle, a hinge or other attachment mechanism that allows the blade to move back and forth relative to the rod. In at least some embodiments, the blade 672 can sweep at least 60, 75, 90, 100, 120, 150, or 180 degrees.

Figure 6A:
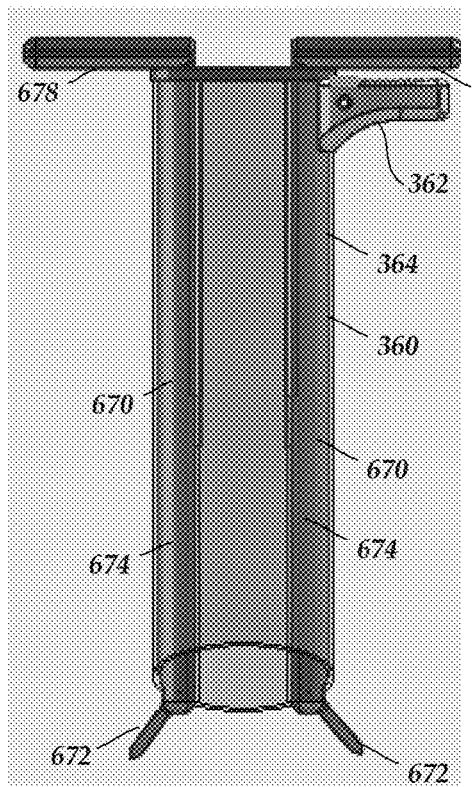
FIG. 6A is a schematic side view of another embodiment of a pair of blade tools inserted into the retractor of FIG. 3A with the blades in an open position, according to the invention.
Figure 6B:
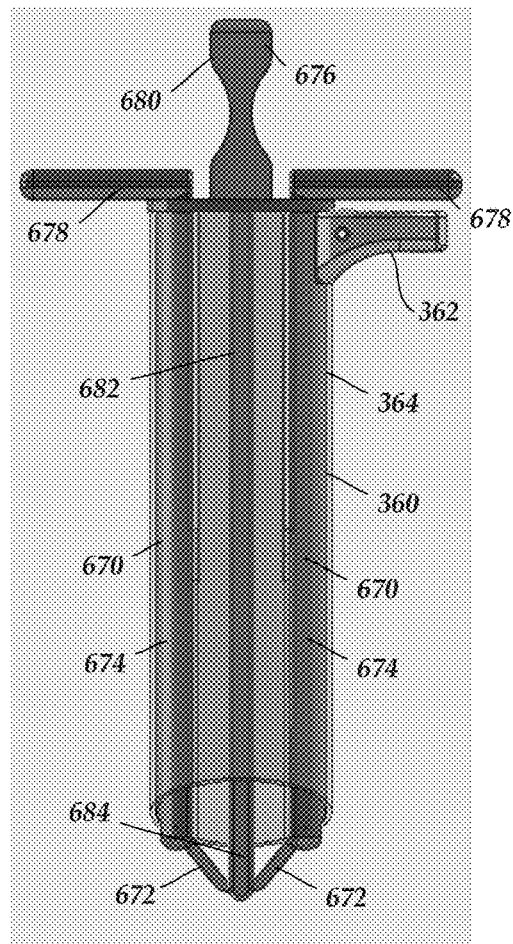
FIG. 6B is a schematic side view of the pair of blade tools and retractor of FIG. 6A and an actuator tool with the blades in a closed position, according to the invention.
Figure 6C:
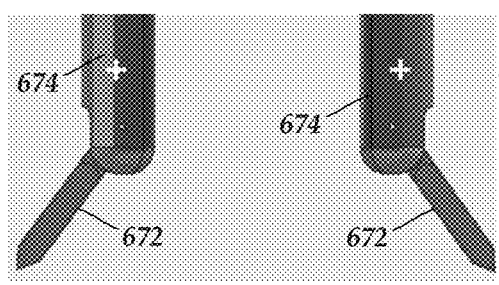
FIG. 6C is a schematic close-up of the blades and rods of the blade tools in FIG. 6A, according to the invention.
Figure 6D:
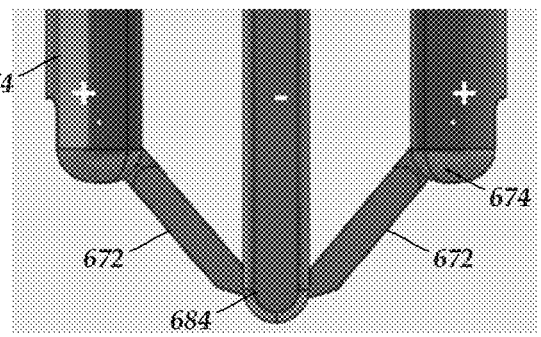
FIG. 6D is a schematic close-up of the blades and rods of the blade tools and the actuator tool in FIG. 6B, according to the invention.

An actuator tool 676 includes a handle 680, a rod 682 and tip 684 and can be inserted into the compartment 358a of the retractor 350. The two blades 672 have the same polarity, as illustrated in FIGS. 6C and 6D, and, in the absence of the actuator tool 676, are repelled from each other, as illustrated in FIGS. 6A and 6C. The tip 684 of the actuator tool 676 has the opposite polarity of the two blades 672 so that when the tip 684 is inserted through the retractor 350, the two blades are attracted to the actuator tool, as illustrated in FIGS. 6B and 6D. Thus, the blades 672 can be moved back and forth by moving the actuator tool 676 up and down, as illustrated in FIGS. 6A-6D.

Figure 8:
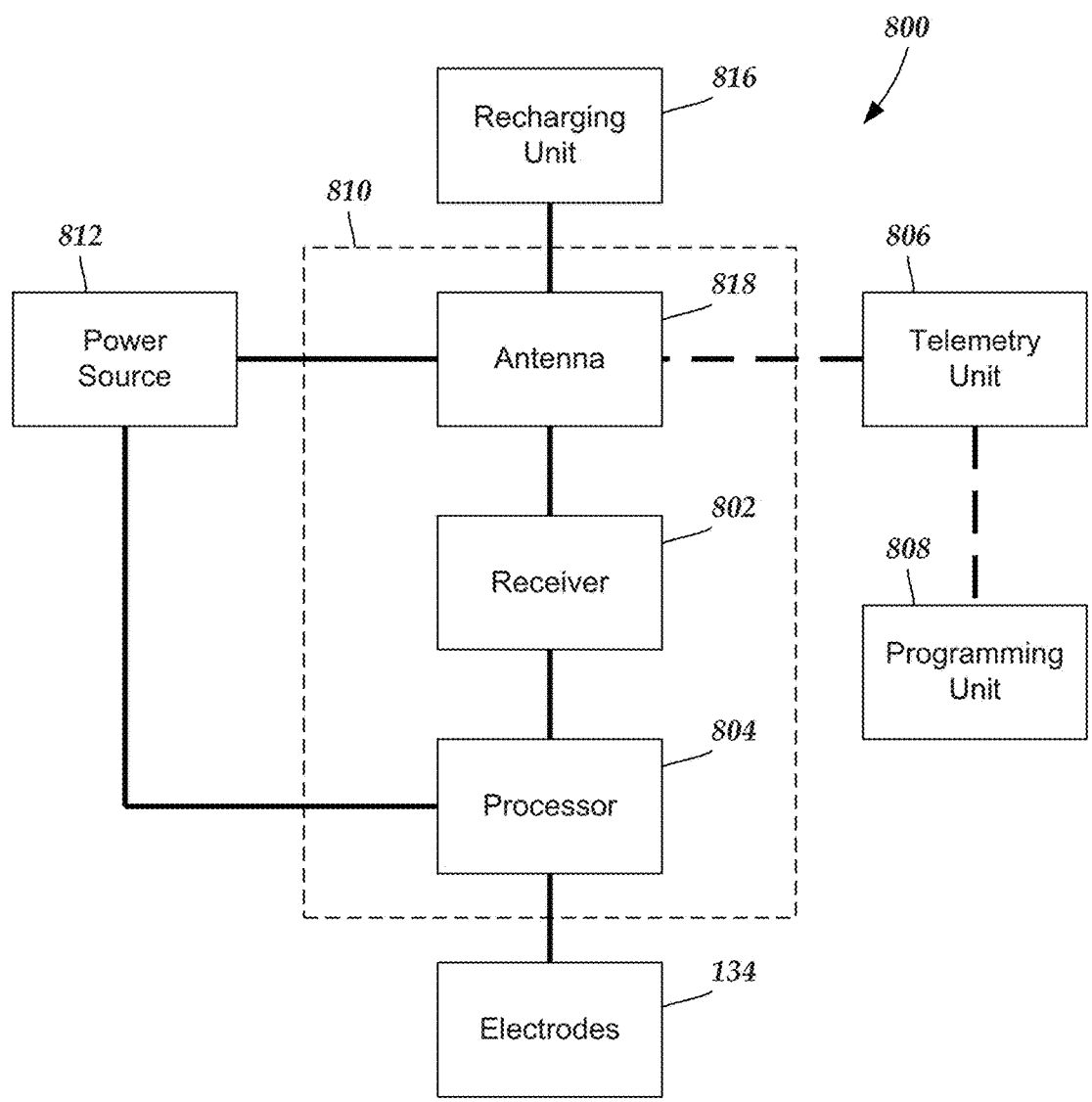
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (fox a power source 812, an antenna 818, a receiver 802, and a processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural-powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 selects which electrode(s) are cathodes and which electrode(s) are anodes. In some embodiments, the processor 804 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by the programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and the receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery in other embodiments, the stimulation system does not include the antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the lever of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantation kit, comprising:
   a retractor for implanting a paddle lead of an electrical stimulation system, the retractor comprising:
      a shaft defining a length, an interior lumen, a first end for receiving tools or the paddle lead, and a second end opposite the first end and configured and arranged for insertion into tissue of a patient;
      a handle coupled to the shaft; and
      at least one divider disposed within the interior lumen and dividing a portion of the interior lumen into at least two compartments, wherein the at least one divider extends from at or near the first end of the shaft and no more than 70% of the length of the shaft; and
   a paddle lead, comprising:
      a paddle body,
      at least one lead body having a distal end portion, a proximal end portion, and a longitudinal length, the distal end portion of each of the at least one lead body coupled to the paddle body,
      a plurality of electrodes disposed in at least two columns on the paddle body,
      a plurality of terminals disposed along the proximal end portion of each of the at least one lead body, and
      a plurality of conductors electrically coupling the plurality of terminals to the plurality of electrodes,
   wherein at least one of the compartments of the retractor is sized for implantation of the paddle lead therethrough.

2. The implantation kit of claim 1, wherein the at least one divider extends at least 40% of the length of the shaft.

3. The implantation kit of claim 1, wherein the at least one divider is two dividers that divide the portion of the interior lumen into three compartments.

4. The implantation kit of claim 3, wherein the three compartments form two side ports and a central port disposed between the two side ports.

5. The implantation kit of claim 4, wherein the central port is larger than either of the two side ports and the central port is sized for implantation of the paddle lead of the electrical stimulation system therethrough.

6. The implantation kit of claim 1, wherein the handle is removable.

7. The implantation kit of claim 1, further comprising a filler configured and arranged for insertion into the shaft of the retractor, the filler comprising a handle and a plurality of filler fingers coupled to the handle and configured and arranged to substantially fill the shaft of the retractor, wherein the filler fingers are separated by at least one gap configured and arranged to align with the at least one divider of the retractor when the filler is inserted into the retractor.

8. The implantation kit of claim 1, further comprising at least one blade tool, each blade tool comprising an actuator, a rod coupled to the actuator, and a blade movably coupled to the rod and configured and arranged to move back and forth in response to the actuator, wherein each blade tool is configured and arranged so that the blade and rod can be inserted through the first end of the shaft into one of the compartments of the shaft of the retractor and the blade can be extended out of the second end of the shaft.

9. The implantation kit of claim 8, wherein the at least one divider is two dividers that divide the portion of the interior lumen into three compartments and the at least one blade tool is two blade tools.

10. The implantation kit of claim 1, further comprising an actuator tool configured and arranged for insertion through the first end of the shaft of the retractor into one of the compartments of the shaft of the retractor; and at least one blade tool, each blade tool comprising a handle, a rod coupled to the handle, and a blade movably coupled to the rod and configured and arranged to move back and forth in response to the actuator tool, wherein each blade tool is configured and arranged so that the blade and rod can be inserted through the first end of the shaft into one of the compartments of the shaft of the retractor and the blade can be extended out of the second end of the shaft.

11. The implantation kit of claim 10, wherein the blade of each of the at least one blade tool has a first magnetic polarity and the actuator tool has a second magnetic polarity opposite the first magnetic polarity.

12. The implantation kit of claim 11, wherein the at least one divider is two dividers that divide the portion of the interior lumen into three compartments and the at least one blade tool is two blade tools.

13. The implantation kit of claim 1, further comprising a control module coupleable to the paddle lead.

14. The implantation kit of claim 1, further comprising a series of introducers, wherein each introducer in the series has a diameter larger than a preceding one of the introducers in the series.

15. A method of implanting an electrical stimulation lead, the method comprising:
providing the implantation kit of claim 1;
inserting the second end of the retractor into tissue of the patient; and
implanting the paddle body of the paddle lead into the patient through one of the at least two compartments of the retractor.

* * * * *